United States Patent [19]
Albini

[11] Patent Number: 4,582,062
[45] Date of Patent: Apr. 15, 1986

[54] HOME TANNING TENT STRUCTURE
[76] Inventor: Mark R. Albini, McCain, N.C. 28361
[21] Appl. No.: 627,783
[22] Filed: Jul. 5, 1984
[51] Int. Cl.[4] .................... A61N 5/06; E04H 15/10; E04H 15/44
[52] U.S. Cl. .................... 128/396; 135/91; 135/106
[58] Field of Search .......... 128/373, 395, 396; 135/91, 102, 105, 106, 113

[56] References Cited
U.S. PATENT DOCUMENTS

| | | | |
|---|---|---|---|
| 1,446,296 | 2/1923 | Irwin | 135/113 |
| 2,210,060 | 8/1940 | Budd | 128/373 X |
| 2,333,915 | 11/1943 | Budd | 135/91 |
| 2,827,065 | 3/1958 | Chapron | 135/106 |
| 3,957,069 | 5/1976 | Denaro | 135/106 X |
| 4,072,158 | 2/1978 | O'Brien et al. | 135/106 X |
| 4,287,554 | 9/1981 | Wolff | 362/294 X |

*Primary Examiner*—Anton O. Oechsle
*Attorney, Agent, or Firm*—Mills and Coats

[57] ABSTRACT

The present invention relates to an apparatus for tanning which may be easily and conveniently used inside the home. The invention employs a tent structure which can be disassembled and stored in a small place and a conventional sunlamp. The interior surfaces of the tent structure are made of a reflective material. The sunlamp is positioned between the reflective surfaces. In use, a person lies in the interior of the structure below the sunlamp. The person receives direct ultraviolet rays from the sunlamp but in addition receives reflected multidirectional ultraviolet rays from the interior reflective surfaces. The reflected rays increase the surface of the skin which may be reached by ulraviolet rays thereby promoting a more even tan.

12 Claims, 3 Drawing Figures

U.S. Patent  Apr. 15, 1986  4,582,062
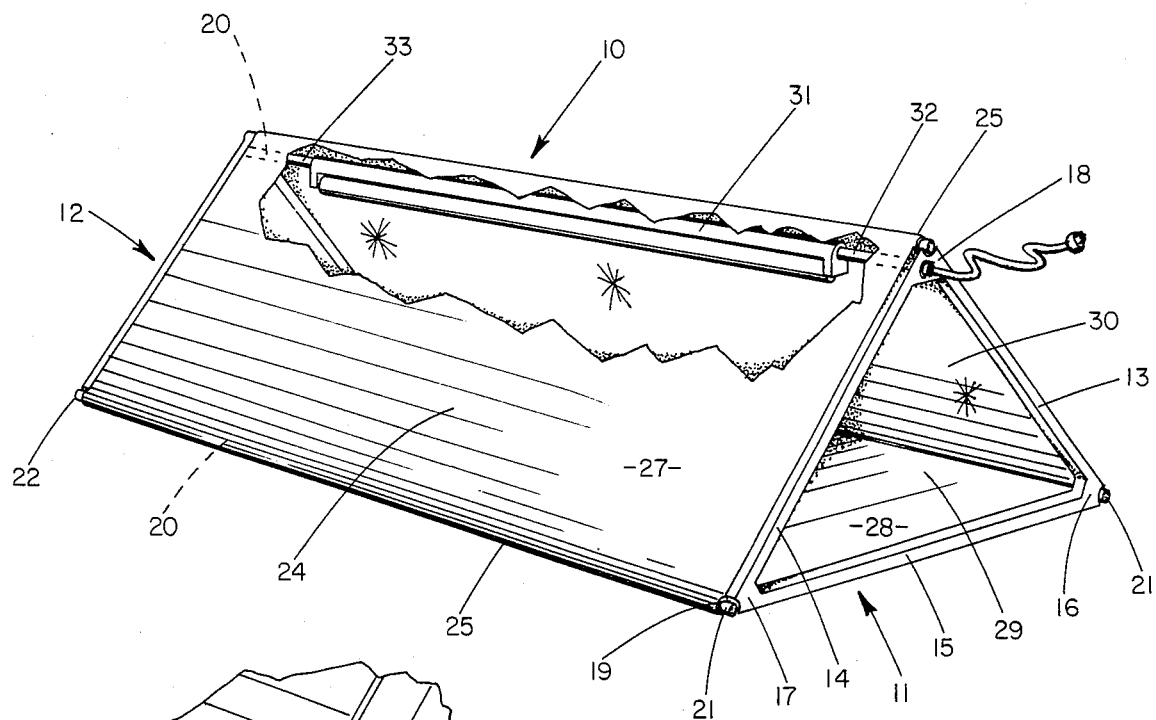
FIG. 1
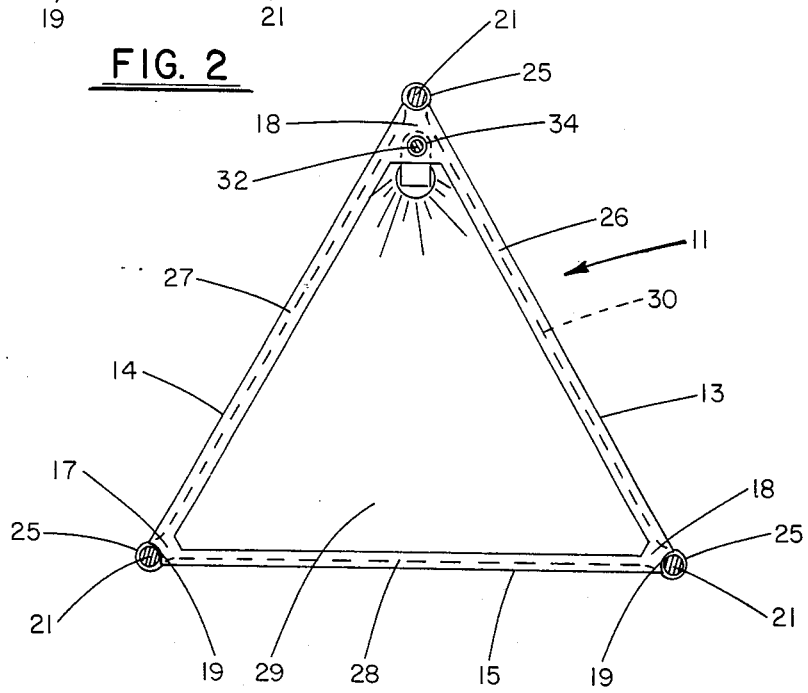
FIG. 2
FIG. 3

HOME TANNING TENT STRUCTURE

FIELD OF INVENTION

The present invention relates to apparatuses for tanning and more particularly to home tanning apparatuses.

BACKGROUND OF INVENTION

Modern American culture views a healthy looking tan as a symbol of beauty. Thus a great deal of time, money and effort is put into achieving and keeping a healthy looking tan. The natural tanning process known as sunbathing can consume hours of one's time each week. Furthermore, because the sun travels across the sky and provides only unidirectional ultraviolet rays, it is difficult to get an even tan by sunbathing. In addition, most climates allow sunbathing only during the summer months creating a necessity for an alternative method for use during the fall and winter months. Commercial tanning facilities solve these problems but not without creating some of their own. For instance, commercial tanning facilities are expensive and in many cases a great distance from the home, particularly to rural residents. Ordinary home sunlamps, while being inexpensive and convenient, are unidirectional and cannot promote an even tan which requires multidirectional ultraviolet rays. Thus, there is a real need for a tanning apparatus which is convenient, inexpensive, efficient and which can provide multidirectional ultraviolet rays.

SUMMARY AND OBJECTS OF INVENTION

The present invention presents an efficient, inexpensive, convenient tanning apparatus which provides multidirectional ultraviolet rays. Particularly, the invention includes an isosceles triangular tent structure with interior reflective surfaces and a sunlamp positioned in the upper interior of the structure between the interior reflective surfaces. Multidirectional ultraviolet rays are directed towards an individual lying within the structure by the sunlamp and by the interior reflective surfaces.

An important objective of this invention is to provide a source for multidirectional ultraviolet rays which can impart an even tan over a greater area of the body than could be achieved through sunbathing or through the use of an ordinary sunlamp alone.

A further object of the present invention is to provide a means for tanning which can be easily and conveniently disassembled and stored in a small area.

It is also an object of this invention to provide an efficient means for tanning which requires only a few minutes a day to achieve and keep a healthy looking tan.

Another object of this invention is to provide a source of ultraviolet rays which will be readily available for use in all seasons.

Still a further object of this invention is to provide convenient and efficient means for tanning which is also inexpensive.

A further object of the present invention is to provide an effective and efficient tanning structure in the form of a tent structure.

Another object of the present invention is to provide a tent type suntanning structure of the character referred to above that can be easily and conveniently assembled and disassembled without the requirement of special tools.

Other objects and advantages of the present invention will become apparent from a study of the following description and the accompanying drawings which are merely illustrative of such invention.

BRIEF DESCRIPTION OF DRAWINGS

FIG. 1 is a perspective view of the tent type tanning structure of the present invention.

FIG. 2 is a fragmentary perspective view illustrating an apex area of a respective tent bracket and further showing a respective rod operatively held about the same apex area.

FIG. 3 is a front or end elevational view of the tent type tanning structure of the present invention.

DESCRIPTION OF INVENTION

With further reference to the drawings, the home tanning tent of the present invention is shown therein and indicated generally by the numeral 10.

Viewing home tanning tent in more detail, it is seen that the same includes a pair of longitudinally spaced triangular tent brackets referred to respectively as front tent bracket 11 and rear tent bracket 12. Tent brackets 11 and 12 include two upstanding members 13 and 14 of equal length which meet at an elevated apex area referred to as upper apex area 18. Base member 15 extends horizontally between and interconnects upstanding members 13 and 14 at lower apex areas 16 and 17. lower apex areas 16 and 17 and upper apex area 18 each contain a curved rod seat 19. It is appreciated that rod seat 19 could actually be a hole bored into each apex area 16, 17 and 18. Upper apex area 18 also contains a light support hole 34 bored therein.

Three tent rods 20 extend between and interconnect front tent bracket 11 and rear tent bracket 12. Each rod includes a front end 21 and a rear end 22. The front end 21 of each rod 20 lies in a respective rod seat 19 on front tent bracket 11. The rear end 22 of each rod 20 lies in a respective rod seat 19 on rear tent bracket 12. Tent brackets 11 and 12 and tent rods 20 thereby form a tent support frame.

The present invention also includes a continuous tent type fabric covering 24 having three parallel open ended hems 25 through which tent rods 20 extend. The area of the fabric covering 24 defined between the open ended hems 25 form upstanding walls 26 and 27 and a tanning floor 28, which in turn define a tanning area 29 about tanning floor 28 between upstanding walls 26 and 27. Upstanding walls 26 and 27 and tanning floor 28 have inner reflective surfaces 30 adjacent to and directed toward tanning area 29.

An elongated sunlamp 31 is secured interiorly within home tanning tent 10 by light support members 32 and 33, which extend from elongated sunlamp 31 to the light support holes 34 in the upper apex area 18 of tent brackets 11 and 12. Sunlamp 31 and light support members 32 and 33 form a sunlamp assembly.

To assemble home tanning tent 10, tent rods 20 are inserted through respective open ended hems 25 such that ends 21 and 22 of each rod 20 extend outwardly from respective hems 25. Tent rods 20 and fabric covering 24 thereby form a tent covering assembly. Tent brackets 11 and 12 are inserted into tent covering assembly 36 by stretching the fabric covering 24 and placing each exposed end 21 and 22 of each rod 20 into a respective rod seat 19 on tent brackets 11 and 12. Finally, sunlamp assembly 35 is secured interiorly within the upper portion of home tanning tent 10 by inserting light support members 32 and 33 into respective light support holes 34 on tent brackets 11 and 12.

Home tanning tent 10 is now ready for use. A person may lie in the tanning area 29. Ultraviolet rays produced by sunlamp 31 are directed downward towards the user by the inner reflective surfaces 30. The result is that the user receives multidirectional ultraviolet rays which impart an even healthy looking tan.

From the foregoing discussion, it is appreciated that the present invention presents a home tanning tent 10 particularly designed to produce multidirectional ultraviolet rays which can be directed towards the user. This exposes a greater area of the body to ultraviolet light resulting in a more even tan. Also of particular significance is the fact that home tanning tent 10 can be easily assembled and disassembled. This enables home tanning tent 10 to be conveniently stored in the home where it will be readily available for use at any time.

It is further appreciated that the present invention is relatively simple and would be easy to manufacture.

The present invention, of course, may be carried out in other specific ways than those herein set forth without departing from the spirit or essential characteristics of the invention. The present embodiments are, therefore, to be considered in all respects as illustrative and not restrictive and all changes coming within the meaning and equivalency range of the appended Claims are intended to be embraced therein.

What is claimed is:

1. A home tanning tent which can be easily and conveniently disassembled and stored in a small place comprising: a pair of longitudinally spaced front and rear triangular tent brackets, each including three apex areas having at least one rod seat and two upstanding sides of equal length which meet at an elevated apex area; at least three elongated tent rods including opposing front and rear ends, wherein the front end of each of said tent rod is detachably secured to a respective rod seat on said front tent bracket and wherein each said tent rod extends longitudinally back from said front tent bracket towards a respective rod seat on said rear tent bracket and wherein the rear end of each said tent rod is detachably secured to a respective rod seat on said rear tent bracket such that each said tent rod extends between and interconnects said front and rear tent brackets; a rectangular fabric covering having an inner reflective surface and provided with open ended hems through which said tent rods extend and which form the upstanding walls of said home tanning tent; at least one sunlamp operatively secured within the upper interior portion between said upstanding walls of said home tanning tent such that ultraviolet rays produced thereby are directed downwardly onto a tanning area defined below said sunlamp and a rectangular fabric floor with an inner reflective surface having open ended hems along two opposite sides through which said tent rods extend.

2. The home tanning tent of claim 1 wherein said front and rear triangular tent brackets include a bottom side extending horizontally between and interconnecting said upstanding sides at lower apex areas.

3. The home tanning tent of claim 2 wherein said bottom side is the same length as said upstanding sides.

4. The home tanning tent of claim 1 wherein said sunlamp is of the elongated type.

5. The home tanning tent of claim 4 wherein said elongated sunlamp is operatively secured to the elevated apex area of each said triangular bracket between said upstanding sides.

6. A home tanning structure which can be easily and conveniently disassembled and stored in a small area comprising: a pair of longitudinally spaced front and rear triangular frames, each including a pair of upstanding sides of equal length; two upstanding rectangular walls with inner reflective surfaces including a front edge and a rear edge, wherein said front edge of each of said rectangular walls is detachably secured to a respective upstanding side of said front tent frame and wherein each of said rectangular walls extend back toward a respective upstanding side of said rear tent frame and wherein said rear edge of said rectangular wall is detachably secured to said rear tent frame such that each of said rectangular walls extends between and interconnects said front and rear tent frames; at least one sunlamp operatively secured within the upper interior portion between said upstanding walls of siad home tanning structure and wherein said front and rear triangular tent frames include a bottom side extending horizontally between and interconnecting said upstanding sides at lower apex areas; and a rectangular floor with an inner reflective surface having a front edge and a rear edge wherein said front edge of said floor is detachably secured to said bottom side of said front tent frame and wherein said floor extends longitudinally towards said rear tent frame and wherein said rear edge of said floor is detachably secured to said bottom side of said rear tent frame such that said floor extends between and interconnects said front and rear tend frames.

7. The home tanning structure of claim 6 wherein said bottom side is the same length as said upstanding sides.

8. The home tanning tent of claim 6 wherein said sunlamp is of the elongated type.

9. A home tanning tent structure defining a tanning area thereunder which can be easily and conveniently disassembled and stored in a small area comprising: a pair of longitudinally spaced end frame structures with each end frame structure including an upper tent support member that extends upwardly from one side of said tent structure to an elevated point and back downwardly to the other side of said tent structure so as to form a pair of upstanding end frame structures; an interconnecting frame structure interconnected between said longitudinally spaced end frame structures so as to form an elevated tent support frame; a tent type fabric covering extending upwardly from one side of said tent structure adjacent said tent suport frame and back downwardly to the other side of said tent structure wherein said tent type fabric covering is supported by said tent support frame so as to form an enclosure above said tanning area and wherein said tent type fabric covering includes a reflective inner surface adjacent to and directed towards said enclosed tanning area; at least one sunlamp operatively secured interiorly within the upper portion of said tent structure such that ultraviolet rays produced thereby are directed downwardly onto said tanning area; and wherein said tent type fabric covering extends across and underneath said tanning area so as to form a floor and wherein said tent type fabric floor includes an inner reflective surface.

10. The home tanning tent structure of claim 9 wherein said front and rear end frame structures include a horizontal base member extending transversely between each side of said tanning area and interconnecting each side of said upper tent support member.

11. The home tanning tent of claim 9 wherein said sunlamp is of the elongated type.

12. The home tanning tent of claim 11 wherein said sunlamp is operatively secured to said tent support frame.

* * * * *